United States Patent [19]

Watson et al.

[11] Patent Number: 4,823,815

[45] Date of Patent: Apr. 25, 1989

[54] TISSUE EXPANDING DEVICE AND METHOD OF MAKING SAME

[75] Inventors: David A. Watson, Goleta; Michele R. Jensen, Montecito; Dennis E. Condon, Santa Barbara, all of Calif.

[73] Assignee: Mentor Corporation, Goleta, Calif.

[21] Appl. No.: 228,841

[22] Filed: Aug. 3, 1988

Related U.S. Application Data

[63] Continuation of Ser. No. 909,223, Sep. 19, 1986, abandoned.

[51] Int. Cl.⁴ .............................................. A61B 19/00
[52] U.S. Cl. .................................. 128/897; 128/344; 604/96; 623/8
[58] Field of Search .......................... 623/7-8; 128/1 R, 344, 844, 847; 604/94, 96

[56] References Cited

U.S. PATENT DOCUMENTS

| | | | |
|---|---|---|---|
| 2,842,775 | 7/1958 | Pangman | 3/36 |
| 3,411,503 | 11/1968 | Hankin | 623/7 |
| 3,600,718 | 8/1971 | Boone | 3/36 |
| 3,663,968 | 5/1972 | Mohl et al. | 3/36 |
| 3,852,833 | 12/1974 | Köneke et al. | 3/36 |
| 3,860,969 | 1/1975 | Arion | 3/36 |
| 3,883,902 | 5/1975 | Lynch | 3/36 |
| 3,919,724 | 11/1975 | Sanders et al. | 623/8 |
| 4,095,295 | 6/1978 | Lake | 3/36 |
| 4,157,085 | 6/1979 | Austad | 623/8 |
| 4,178,643 | 12/1979 | Cox, Jr. | 3/36 |
| 4,205,401 | 6/1980 | Frisch | 623/8 |
| 4,263,682 | 4/1981 | Bejarano | 3/36 |
| 4,428,364 | 1/1984 | Bartolo | 128/1 R |
| 4,455,691 | 6/1984 | Von Aken Redinger et al. | 628/8 |
| 4,470,160 | 9/1984 | Covon | 623/8 |
| 4,574,780 | 3/1986 | Monders | 623/8 |
| 4,685,447 | 8/1987 | Iversen et al. | 623/8 |

Primary Examiner—Stephen C. Pellegrino
Assistant Examiner—Mark F. Colosimo
Attorney, Agent, or Firm—Kinney & Lange

[57] ABSTRACT

A tissue expanding device includes a substantially non-extensible base and a top layer joined to the periphery of the base such that the base and the expansion layer are in contact with each other when the device is in a non-expanded state. In the non-expanded state, the device has a thickness substantially equal to the thickness of the combined thickness of the base and expansion layer.

4 Claims, 3 Drawing Sheets

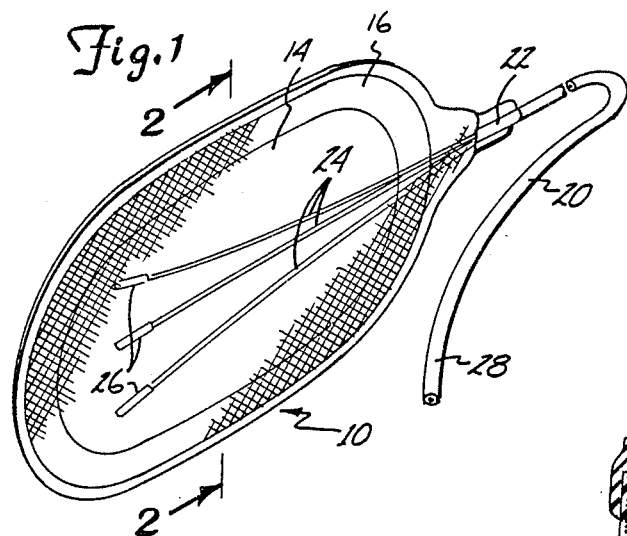
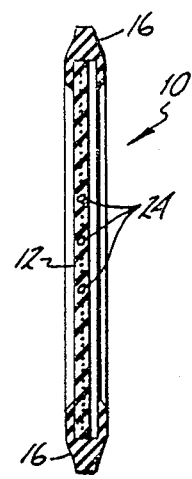
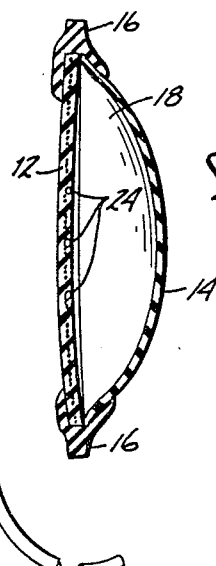
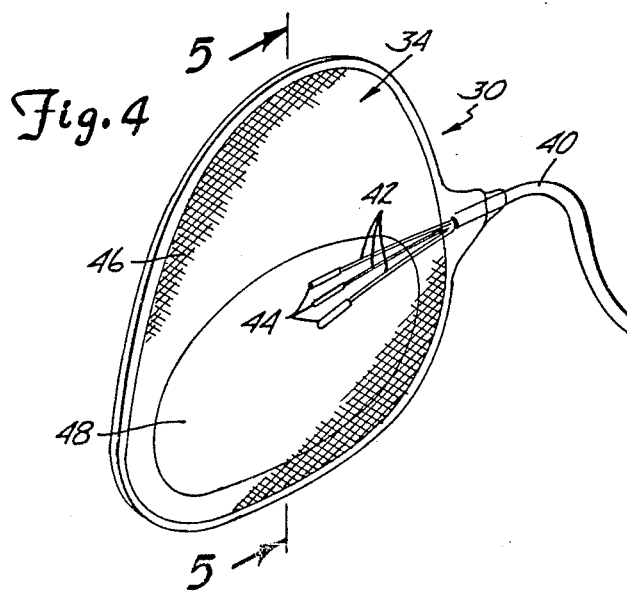
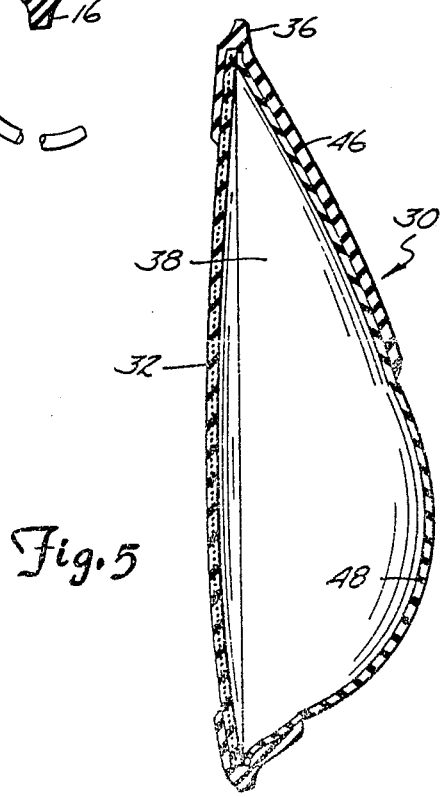

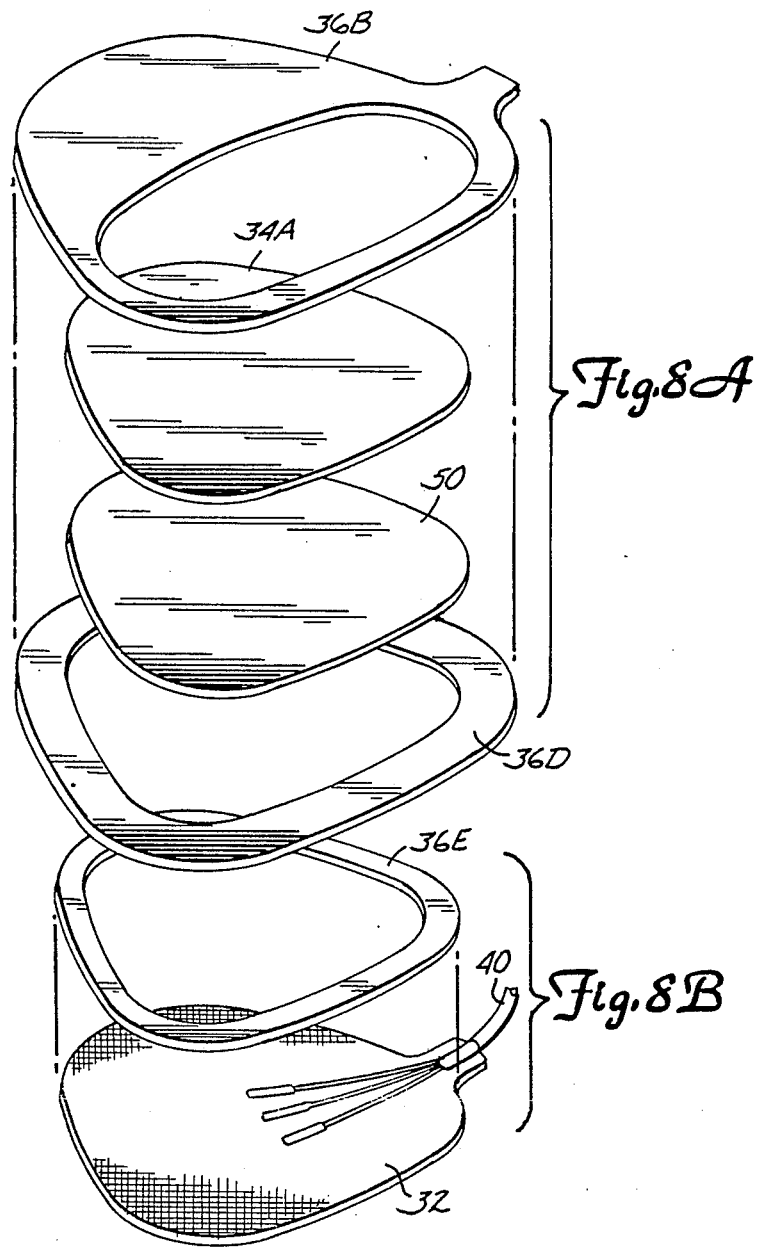

TISSUE EXPANDING DEVICE AND METHOD OF MAKING SAME

This is a continuation of application Ser. No. 06/909,223, filed Sept. 19, 1986 (now abandoned).

BACKGROUND OF THE INVENTION

1. Field of the Invention

The present invention relates to tissue expansion devices, in particular, it relates to a substantially flat skin expander that is substantially flat when in a non-expanded state and to methods of making such a skin expander.

2. Description of the Prior Art.

Expansion of skin and subcutaneous tissue by implantation of expandable devices have received great acceptance. Such devices develop an expanded layer of skin that is to be used on a recipient area of a patient. Such devices have also been used to expand breasts to develop a cavity to receive a breast prosthesis. Skin expanders have also been used in reconstructive breast surgery, expanding the reconstructed site so that a breast prosthesis can be implanted.

As in all surgical procedures, it is desirable to make the expander implant procedure as least obtrusive to the patient as possible. In implanting a skin expander, an incision is made through the skin and the subcutaneous tissue. The skin expander is then placed between the subcutaneous tissue and muscle or bone, depending on the area of the body in which the skin expander is implanted. It is desirable to make the incision as small as possible so that the implantation of the skin expander is as inobtrusive as possible to the patient.

The Radovan et al U.S. Pat. No. 4,217,889 and the Austad U.S. Pat. No. 4,157,085 illustrate conventional skin expanders. Such skin expanders have a base and an expansion cover attached to the base. The expansion cover is spaced from the base even when the skin expander is in a non-expanded state. To insert such a skin expander beneath the subcutaneous tissue, an unnecessarily large incision must be made in order to insert the skin expander Alternatively, the skin expander could be folded and inserted through a smaller incision. However, upon expansion, the skin expander may not unfold in the manner desired causing problems during expansion.

One type of mammary prosthesis also includes an expandable chamber. Examples of such prostheses are disclosed in the following patents:

| Inventor | Patent No. |
| --- | --- |
| Bejarano | 4,263,682 |
| Mohl et al | 3,663,968 |
| Koneke et al | 3,852,833 |
| Pangman | 2,842,775 |
| Lake | 4,095,295 |
| Bartolo | 4,428,364 |
| Cox, Jr. | 4,178,643 |
| Lynch | 3,883,902 |
| Arion | 3,860,969 |
| Boone | 3,600,718 |

All of the breast prostheses described in the above-mentioned patents require a larger than necessary incision since the breast prostheses, in their expanded state, include an expansion chamber prior to being filled with a fluid.

SUMMARY OF THE INVENTION

The present invention includes a skin expanding device having a substantially non-extensible base and a top expansion layer joined to the periphery of the base to define an expansion chamber when fluid is introduced between the base and the expansion layer. The expansion layer is joined to the base such that the layer is in contact throughout substantially its entire area with the base when the device is in a non-expanded state to form a flat skin expander. When the skin expander is in a non-expanded state, the thickness of the expander is substantially equal to the combined thicknesses of the base and the expansion layer.

In another aspect of the present invention, the expansion layer has a thick non-expanding portion and a thin expanding portion such that when the expander is being filled with fluid, the thinner portion expands proportionally more than the thicker portion in a controlled selected manner resulting in a directional expansion of skin.

BRIEF DESCRIPTION OF THE DRAWINGS

FIG. 1 is a perspective view of the skin expander of the present invention.

FIG. 2 is a cross-sectional view of the expander of FIG. 1 taken along the line 2—2 of FIG. 1.

FIG. 3 is a sectional view of the skin expander of FIGS. 1 and 2 in an expanded state.

FIG. 4 is a perspective view of an alternative embodiment of the skin expander of the present invention.

FIG. 5 is a cross-sectional view of the skin expander of FIG. 4 taken along the line 5—5 in FIG. 4.

FIGS. 8A and 8B are exploded views of still another method of making the skin expander of the present invention.

DETAILED DESCRIPTION OF THE PREFERRED EMBODIMENTS

Figure 6:
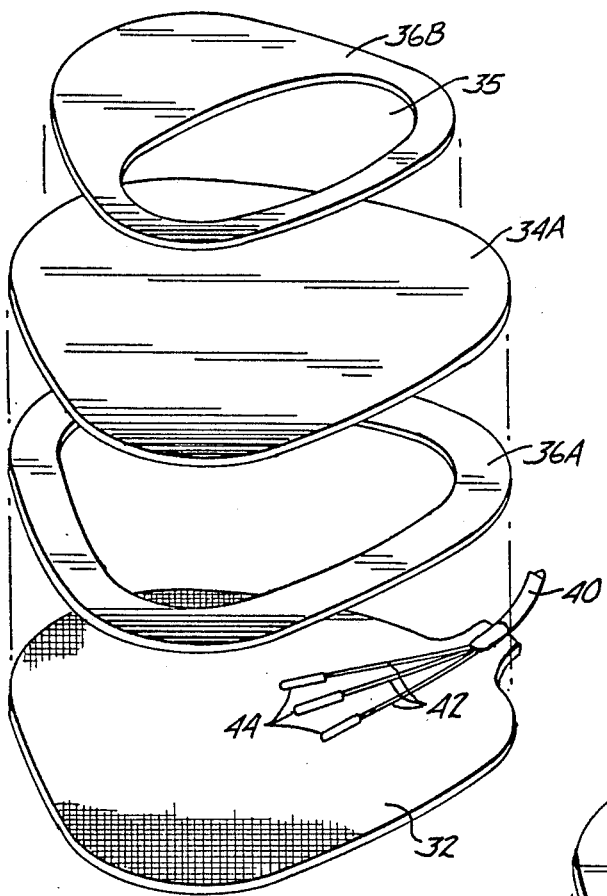
FIG. 6 is an expanded perspective view illustrating one method of making the skin expander of the present invention.

The skin expander of the present invention is generally indicated at 10 in FIGS. 1 and 2. Throughout the figures like references characters will be used to indicate like elements. The skin expander 10 includes a base 12, an expansion layer 14 and joined overlapping washers 16 joining the base 12 and the expansion layer 14 to form an expansion chamber 18, as illustrated in FIG. 3.

A fill tube 20 provides a passage for fluid, such as saline fluid, to be forced into the expansion chamber 18. The fill tube 20 has an end portion 22 that extends between the base 20 and the expansion layer 14. A plurality of fluid supply passages 24 are provided in the base and communicate with the end portion 22 of the fill tube 20 and extend through the base to wells 26 which communicate with the chamber 18. The tube 20 at an opposite end 28 is in fluid communication with an injection site (not shown) such as described in the Radovan et al U.S. Pat. No. 4,217,889, which is incorporated herein by reference. The particular type of injection site is not important to the present invention. Other types of injection sites can be used with the present invention.

The base 12, expansion layer 14 and overlapping washers 16 are preferably made of a medical grade elastomer, such as silicone rubber.

The base 12 is substantially non-extensible. By substantially non-extensible, it is meant that the base retains its area shape and does not expand, such as the expansion layer 14. To make the base substantially non-extensible, the base is made of such a thickness that the fluid forces inside the chamber 18 do not stretch or extend the base 12 while extending or stretching the expansion layer 14. In addition, a Dacron ® mesh is provided, preferably, throughout the entire area of the base 12 to prevent the base from expanding.

An important aspect of the present invention is that the device 10 is substantially flat prior to inflation, as clearly illustrated in FIG. 2. By substantially flat is meant that the expansion layer 14 is in contact with the base 12 throughout substantially its entire area such that the cross-sectional thickness of the expander is substantially equal to the combined thicknesses of the base and the expansion layer in the expansion area of the skin expander.

The flat tissue expander of the present invention eliminates "dog-ears" that have resulted from using prior art skin expanders. "Dog-ears" occur during expansion and from a folded skin expander not expanding properly. "Dog-ears" have been known to puncture the subcutaneous tissue and skin during expansion.

The device 10 of the present invention is a substantial improvement over the prior art skin expanders, such as described in the Radovan et al U.S. Pat. No. 4,217,889 and the Austad U.S. Pat. No. 4,157,085. As described in the Radovan et al Patent, the expander is not flat when in a non-expanded state since the expander contains random wrinkles or even concentric rings, much like bellows. In Austad, the expansion envelope contains a material which establishes an osmotic potential across the envelope wall thereby making the expansion envelope not flat. Both of these types of expanders require an incision that is unnecessarily large for insertion of the expander between the skin and subcutaneous tissue layer. In contrast, the device of the present invention requires a minimal incision due to its substantially flat cross-section making insertion of the device beneath the subcutaneous tissue as unobtrusive as possible.

An alternative embodiment of the present invention is generally indicated at 30 in FIGS. 4 and 5. The embodiment 30 is a directional skin expander, that is, one portion of the expansion envelope expands proportionally more than another portion. One use for such a directional skin expander is in breast expansion. Skin expanders are used to expand breasts so that a breast prosthesis may then be subsequently implanted under the expanded tissue. For cosmetic purposes, breast prostheses are shaped to conform to the natural contour of a breast. Conventional skin expanders expand outwardly uniformly, creating a round cavity under the subcutaneous tissue. Consequently, the breast must be overexpanded so that a breast prosthesis can be inserted into the cavity with minimal problems.

The directional skin expander of the present invention provides for expansion such that the breast need not be overexpanded to accommodate the breast prosthesis. Similar to the embodiment 10 of FIGS. 1-3, the embodiment 30 is a substantially flat skin expander that permits insertion of the embodiment 30 beneath the subcutaneous tissue with a minimal incision and insertion beneath the tissue in a least obtrusive manner.

The embodiment 30 includes a substantially non-extensible base 32 and an expansion layer 34 joined together by joined overlapping washers 36 to define an expansion chamber 38. A fill tube 40 provides a passage for inflation fluid, such as saline fluid, for inflation of the chamber 38. A plurality of fluid passages 42 are in fluid communication with the fill tube 40 and extend through the base 32. A plurality of wells 44 disposed within the base provide fluid communication between the passages 42 and the chamber 38. Similar to the fill tube 28, the fill tube 40 is connected to an implantable injection site (not shown) such as described in the Radovan et al U.S. Patent.

The expansion layer 34 includes a thick section 46 and a thin section 48. When the skin expander is filled with fluid, both the thick and thin sections stretch outwardly with the thin sections stretching proportionally more than the thick section, as illustrated in FIG. 5. In one working embodiment, the thin section was $0.030 \pm 0.002$ inches thick, while the thick section was approximately $0.055 \pm 0.004$ inches thick. A suitable relative range of thicknesses of the thick section to the thin section is approximately 50% to 300%. A preferred relative range is that the thick section is twice as thick as the thin section. The rate of stretching of the thin section to the thick section is controlled by the relative thickness of the thin section in relation to the thick section. In addition, stretching can also be controlled by making the thin section of one type of silicone rubber and the thick section of another type of silicone rubber or of another type of elastomeric material.

Figure 7:
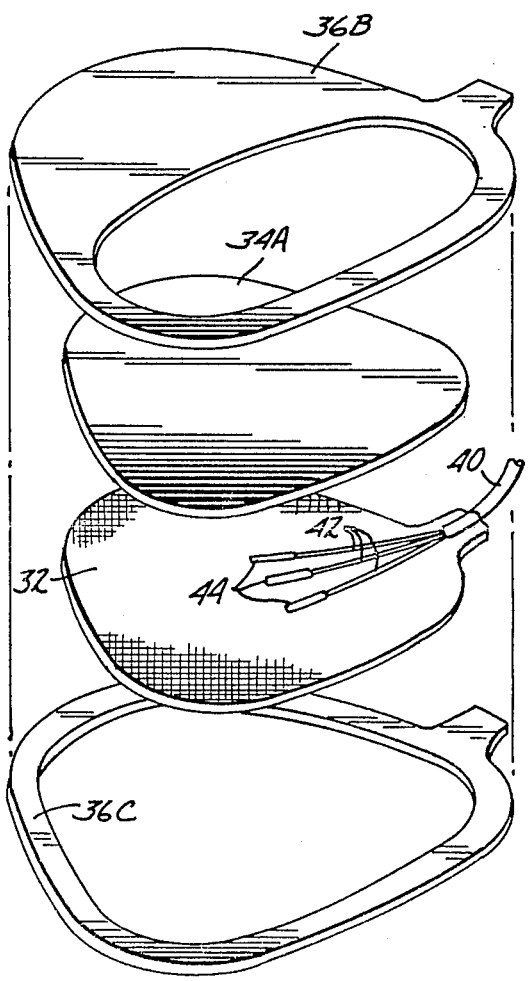
FIG. 7 is an exploded view of another method of making the skin expander of the present invention.

FIGS. 6, 7 and 8 illustrate several methods of making the skin expander of the present invention. Although FIGS. 6, 7 and 8 illustrate the making of the specific directional skin expander of FIGS. 4 and 5, it will be understood that the skin expander illustrated in FIGS. 1-3, although different in shape, is produced in substantially the same manner.

Referring to FIG. 6, in which a first method is illustrated, the expander is formed by positioning an unvulcanized washer 36A between the base 32 and an expansion sheet 34A and a second upper unvulcanized washer 36B. The unvulcanized washer 36A is configured as a ring having substantially the same outer diameter and shape as the expansion sheeting 34A and the base 32. An end of the fill tube 40 is formed within the base 32 such that it communicates with the fluid passages 42 of the base.

The washer 36B and the sheet 34A form the expansion layer 34 illustrated in FIGS. 4 and 5. The washer 36B is only required in the working embodiment when a directional expansion is desired.

The washer 36B has an opening 35 so that when the washer 36B and the sheet 34A are joined they provide a thin and thicker area in the expansion layer. The washer 36B, the sheeting 34A, the washer 36A and the base 32 are positioned in contact with each other and the washers 36B and 36A are then vulcanized, adhesively joining all the elements illustrated in FIG. 6.

Referring to FIG. 7, wherein an alternative method of forming the expander is shown, a bottom washer 36C is positioned beneath the base 32 and the top washer section 36B is positioned above the expansion sheet 34A. The top washer section 36B and the expansion sheet 34A form the expansion layer 34 illustrated in FIGS. 4 and 5. To provide the expansion layer 14 of FIGS. 1-3, the washer 36B is configured as a ring similar to washer 36C. The base 32 has fluid passages 42, wells 44 and tube 40 previously formed therein.

The base 32 and the sheet 34A are formed of vulcanized silicone elastomer. The bottom washer section 36C and the top washer section 36B are made of unvulcanized silicone rubber. The bottom and top washers 36C and 36B are slightly larger in diameter, approximately one-eighth inch (⅛"), than the sheeting 34A and base 32 such that the washers overlap the perimeter of the base and sheeting 32 and 34A. The washer section 36C, the base 32, the sheet 34A and the washer 36B are positioned in contact with each other and vulcanized. The bottom washer section 36C and the top washer section 36B are cohesively joined to each other retaining the sheeting 34A and the base 32 to form a fluid-tight chamber. Vulcanizing further joins the washer 36B and the sheeting 34A to form the expansion layer.

A preferred alternative method of making the device of the present invention is illustrated in FIGS. 8A and 8B. The method illustrated in FIGS. 8A and 8B is a two-step method.

The first step includes positioning the sheeting 34A and a backing sheet 50 between the top washer 36B and a ring-type washer 36D. The backing sheet 50 is of the same area shape as the expansion sheeting 34A and is positioned between the expansion sheeting 34A and the washer-ring 36D. The washers 36B and 36D are approximately one-eighth inch (⅛") larger in size along the perimeter than the expansion sheeting 34A and the backing sheet 50. The washer 36B, the expansion sheeting 34A, the backing sheet 50 and the washer 36D are placed in contact with each other and vulcanized to form a unitary piece.

The backing sheet 50 is then removed from contact with the expansion sheeting 34A. The backing sheet 50 is made of a material, such as Delrin ®, which is not capable of being joined by the washers 36B and 36D during vulcanization.

The second step of the method includes joining the previously-formed unitary piece to the base 32. The previously-formed unitary piece is joined to the base 32 by an unvulcanized washer 36E that is disposed between the unitary piece and the base 32. The unitary piece, the washer 36E and the base 32 are placed in contact with each other and vulcanized to produce a flat skin expander.

Although the present invention has been described with reference to preferred embodiments workers skilled in the art will recognize that changes may be made in form and detail without departing from the spirit and scope of the invention.

What is claimed is:

1. A skin expanding device comprising:
   a substantially non-extensible base;
   an expansion layer joined to the periphery of the base defining an expansion chamber when fluid is introduced between the base and the expansion layer;
   means for introducing fluid between the base and the expansion layer; and
   wherein the expansion layer includes only first and second area portions, the first area portion being 50% to 300% thicker than the second area portion such that when fluid is introduced between the expansion layer and the non-extensible base, the first area portion expands proportionally differentially from the second area portion, both area portions expanding as fluid is being introduced, the expansion layer and base initially being flat in a non-expanded state so that the expansion layer is in contact with the base throughout the layers' entire area so that neither base nor layer has any folds or wrinkles when in the non-expanded state.

2. The device of claim 1 wherein the first portion expands at a proportional rate with respect to the second portion.

3. The device of claim 1 wherein the means for introducing fluid is a fill tube fluidly communicating with the chamber.

4. The device of claim 1 wherein the means for introducing fluid is an injection site in fluid communication with the chamber.

* * * * *